United States Patent
Munetaka et al.

(10) Patent No.: US 9,797,915 B2
(45) Date of Patent: Oct. 24, 2017

(54) ANALYZING SYSTEM

(71) Applicants: Keisuke Munetaka, Kyoto (JP); Toshinobu Yanagisawa, Kyoto (JP)

(72) Inventors: Keisuke Munetaka, Kyoto (JP); Toshinobu Yanagisawa, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 14/020,039

(22) Filed: Sep. 6, 2013

(65) Prior Publication Data
US 2015/0073725 A1    Mar. 12, 2015

(51) Int. Cl.
G01N 35/00 (2006.01)
G01N 30/24 (2006.01)
G01N 30/86 (2006.01)
G01N 30/84 (2006.01)
G01N 30/00 (2006.01)
B01D 15/08 (2006.01)

(52) U.S. Cl.
CPC ......... *G01N 35/0092* (2013.01); *G01N 30/24* (2013.01); *G01N 30/8658* (2013.01); *G01N 35/00871* (2013.01); *B01D 15/08* (2013.01); *G01N 30/00* (2013.01); *G01N 30/84* (2013.01); *G01N 2035/0094* (2013.01)

(58) Field of Classification Search
USPC .......................................................... 702/23
See application file for complete search history.

(56) References Cited

U.S. PATENT DOCUMENTS

2012/0018100 A1*  1/2012  Iwata et al. ................. 159/4.01
2013/0014566 A1*  1/2013  Marks ......................... 73/61.55

FOREIGN PATENT DOCUMENTS

JP    2004-101198 A    4/2004
JP    2006525509 A    11/2006
WO    WO-2004098739 A2    11/2004

OTHER PUBLICATIONS

Examination Report Received for Japanese Patent Application No. 2011-035601, dated Nov. 25, 2014, 4 pages (2 pages of English Translation and 2 pages of Official Copy).

(Continued)

*Primary Examiner* — Paul D Lee
(74) *Attorney, Agent, or Firm* — Morgan, Lewis & Bockius LLP

(57) ABSTRACT

In an analyzing system including a commanding unit for sending a command and an executing unit for executing a processing upon receiving the command, a processing instruction may not be executed at the right time due to a heavy traffic of information and other factors. In order to solve this problem, in a preparative separation system 1 according to the present invention, a PC 20 provides the execution time for starting/finishing the fractionation processing to a controller 18. Therefore, even in the case where the time of the PC 20 and that of the controller 18 are not synchronized, the controller 18 can accurately set the execution time for starting/finishing the fractionation in a preparative separation unit 16. A piping 17 may be placed so that the traveling time of sample components is sufficiently larger than the delay time of signals due to the signal transfer lag and other reasons. This can absorb the delay time, allowing the units to cooperate with each other at a correct timing.

1 Claim, 3 Drawing Sheets

(56) References Cited

OTHER PUBLICATIONS

Japanese office action mailed Mar. 4, 2014 for the corresponding Japanese Patent Application No. 2011-035601 and the English translation of "Reason for Rejection".
Examination Report Received for Japanese Patent Application No. 2011-035601 dated Feb. 17, 2015, 3 pages (1 page of English Translation & 2 pages of Official copy).

* cited by examiner

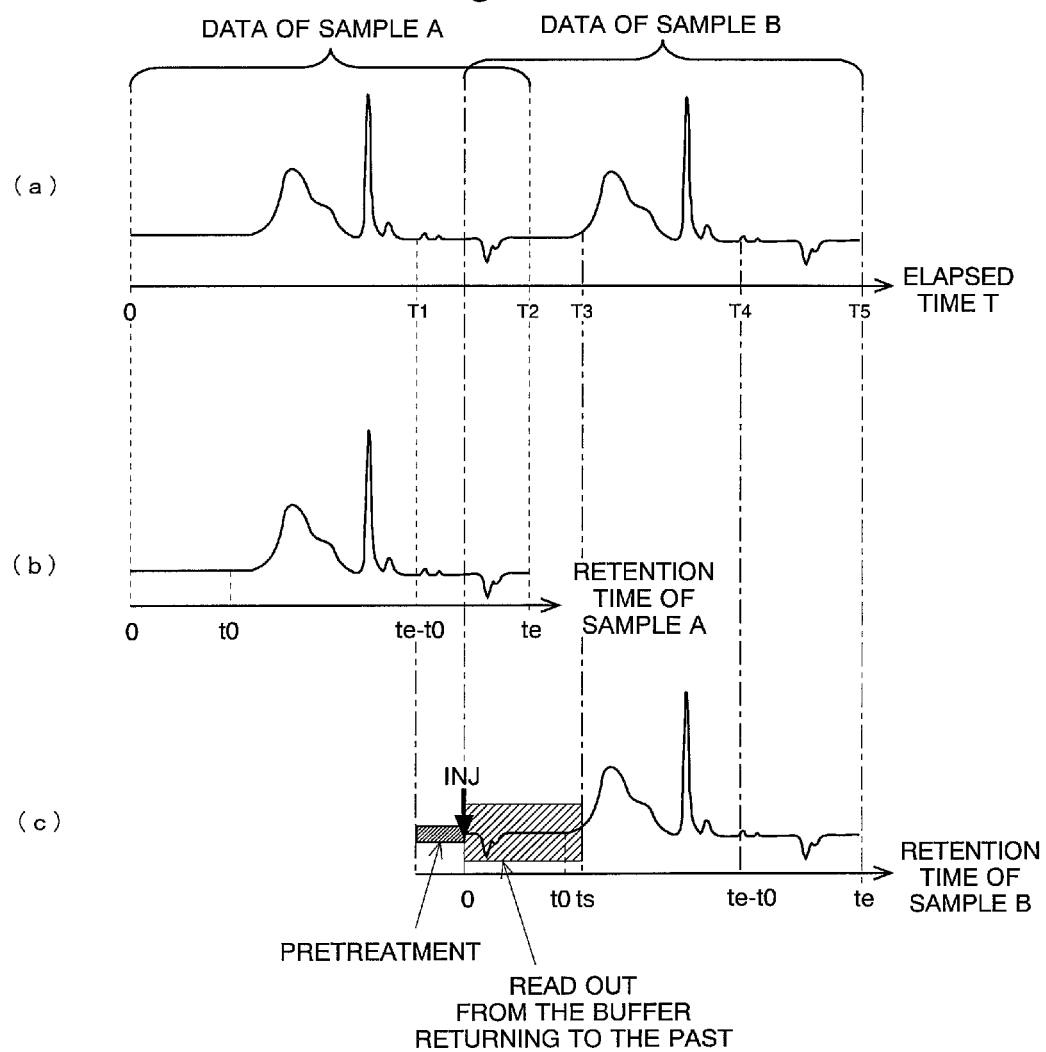

ANALYZING SYSTEM

TECHNICAL FIELD

The present invention relates to an analyzing system including a unit for sending a command and a unit for performing, upon receiving the command, a predetermined processing.

"Analyzing systems" mentioned in the present invention may have any kind of structure and configuration as long as they have a function for measuring a physical quantity or physical quantities of a sample to be measured.

BACKGROUND ART

Generally, an analyzing system such as a liquid chromatograph analyzing system is not composed of only an analyzing unit which has a liquid supplier, a column, a detector, and other units. It is usually a combination of a plurality of units including an analyzing unit, a control unit for controlling the analyzing unit, a data processing unit for receiving the signals provided from a detector and analyzing them and for creating a chromatogram with the elapsed time assigned to the horizontal axis and the relative signal intensity to the vertical axis (for example, refer to Patent Document 1).

Configuring the system by combining independent units as in the aforementioned case facilitates the maintenance of each unit, compared to the system in which all the units are unified. In addition, with this configuration, it is relatively easy to combine different kinds of units. This has the advantage that the configuration of the product can be easily modified to suit the needs of the user. Furthermore, as long as the units are connected to each other, each unit composing the analyzing system can be placed in physically different places.

In the case where a plurality of units are included in an analyzing system and they cooperate to perform some kind of processing, one unit among them functions as a commanding unit and another unit functions as an executing unit so as to cooperate with each other to perform the processing. For example, in a preparative separation system in which a sample separated by a chromatograph is fractionated into components, a fractionation operation is performed by the cooperation of a detector for detecting the sample components eluted from the chromatograph and a control unit for instructing, upon receiving the detection signal, a preparation unit to fractionate the sample. In an overlap injection data collection system in which a next sample is injected while one sample is being analyzed by a chromatograph, multiple units cooperate with each other. Such units include a detector for detecting the sample components eluted from the chromatograph, a data processing unit for performing, upon receiving the detection signal, a data processing such as a peak detection and analysis, and a control unit for providing an instruction for injecting a sample into the chromatograph.

BACKGROUND ART DOCUMENT

Patent Document

[Patent Document 1] JP-A 2004-101198

DISCLOSURE OF THE INVENTION

Problem to be Solved by the Invention

In any conventional analyzing apparatus, a unit for providing an instruction sends the instruction to an execution unit at the point in time when the execution unit executes the operation indicated by the instruction. For example, in the case of the preparative separation system, which has been previously described as the first example, the controlling unit sends a fractionation initiation signal and a fractionation termination signal respectively at the point in time when the preparative separation unit starts and finishes the fractionation process. In the case of the overlap injection data collection system, which has been previously described as the second example, the data processing unit receives a data processing initiation signal from the chromatograph at the point in time when the next sample is injected into the chromatograph, and starts a data processing relating to the sample.

However, sending an instruction at the point in time of process execution as just described has a variety of problems. For example, in the case of the aforementioned preparative separation system, the controlling unit receives a detection signal from the detector, determines the point in time of starting/finishing the fractionation based on the level of the detection signal, the shape of an upslope or downslope, and then sends out an operation instruction. In this operation, the initiation or termination of the fractionation in the preparative separation unit may not be performed at the correct time (i.e. the precise point in time when the component to be analyzed arrives at the preparative separation unit) because the period of time required to receive the detection signal from the detector and that to send an operation instruction to the preparative separation unit are not constant depending on the state of the load of the entire system and the communication traffic.

In the case of the overlap injection data collection system, the data processing unit performs a series of data processing operations for one sample: e.g. creating a data file, collecting the data, saving the data file, analyzing the data, and outputting a report. However, starting a data processing of the next sample while performing a data-processing of the current sample complicates the processing flow and places great stress on the CPU.

Means for Solving the Problem

To solve the aforementioned problem, the present invention provides an analyzing system including:

a commanding unit for sending a command; and an executing unit for, upon receiving the command, executing a processing, wherein the commanding unit computes a shift time which is a difference between a predetermined base-point time in the executing unit and an execution time of the processing for which the command is sent to the executing unit, and sends the computed shift time with the command for the processing to the executing unit, and the executing unit executes, at a point in time before or after the base-point time by the shift time, the processing indicated by the command received with the shift time.

In the analyzing system according to the present invention, the commanding unit instructs the execution unit to execute a processing, designating a relative time (i.e. the shift time). The shift time may be a positive value or a negative value. The execution unit computes the point in time by adding the shift time to the base-point in time and then executes the instructed processing at the computed point in time. The computed point in time will be after the base-point time in the case where the shift time is a positive value, while it will be before the base-point time in the case where the shift time is a negative value.

Determining the point in time when a processing is executed in the execution unit by taking into account the shift time from the base-point in time of the execution unit as just described allows the execution unit to accurately set the execution time of the instructed processing even if the time of the commanding unit and that of the execution unit are not synchronized. In addition, using a sufficiently long shift time can eliminate the possibility of being affected by the signal communication delay and other factors.

In the analyzing system according to the present invention, a processing instruction is provided to the execution unit designating the execution time of the processing. Therefore, a variety of processings may be executed in a distributed manner by the execution unit. This decreases the load on the CPU of the execution unit.

Effects of the Invention

With the present analyzing system according to the present invention, the commanding unit instructs the execution unit to execute a processing, designating a relative time. Hence, even in the case where the time of the commanding unit and that of the execution unit are not synchronized, the execution unit can accurately set the point in time when the instructed processing is to be executed. In addition, with the present analyzing system according to the present invention, it is possible to eliminate the influence of a signal communication delay and other factors and execute a variety of processings in a distributed manner in the control unit and the data processing unit. This allows more flexible system design.

BRIEF DESCRIPTION OF THE DRAWINGS

FIG. 3 is a diagram explaining the data collection operation by the analyzing system of the second embodiment.

BEST MODES FOR CARRYING OUT THE INVENTION

The analyzing system according to the present invention can be applied to various kinds of analyzing systems. Hereinafter, two specific examples are described. In the first embodiment, the analyzing system according to the present invention is applied to a preparative separation system, and in the second embodiment, it is applied to an overlap injection data collection system.

First Embodiment

Figure 1:
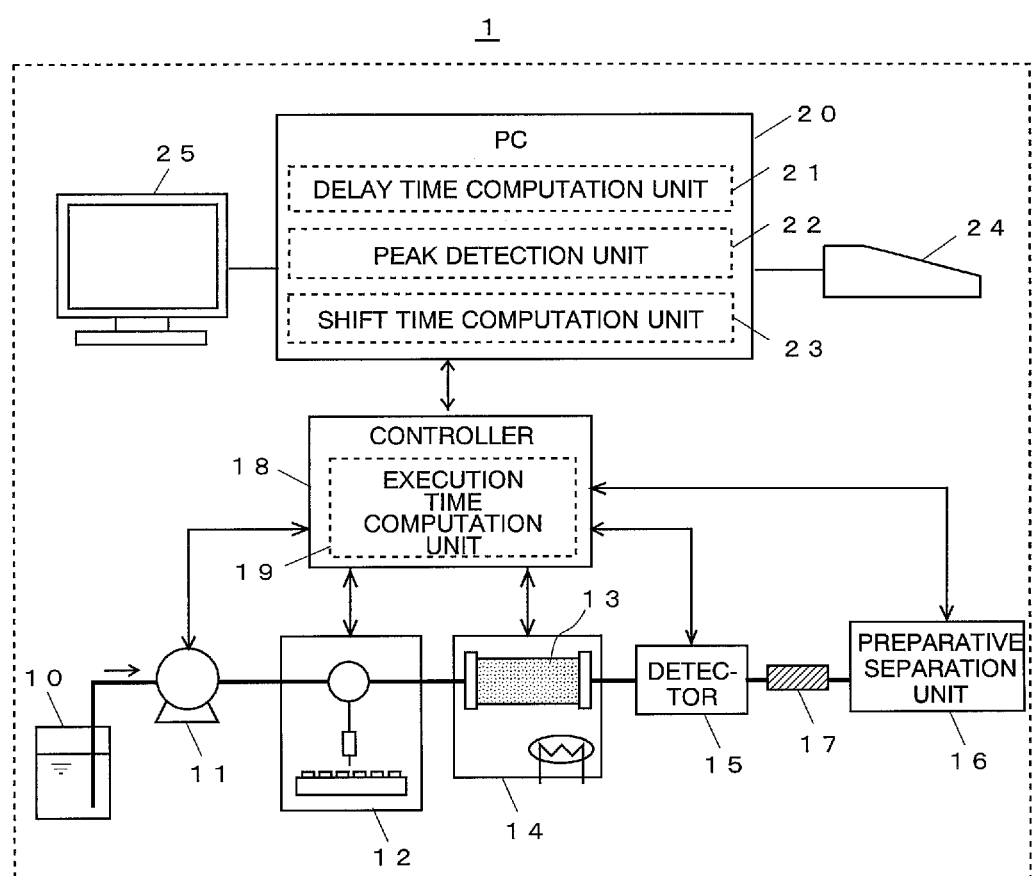
FIG. 1 is a schematic configuration diagram of the main components of the first embodiment of the analyzing system according to the preset invention.

FIG. 1 is a schematic diagram of the main components of the preparative separation system 1 according to the present embodiment.

The preparative separation system 1 includes, as the units for preparative operations: a supply pump 11 for sucking a mobile phase (or a carrier) from a mobile phase container 10 and sending it out at a constant flow rate; an auto sampler for selectively collecting samples in a predetermined order from a number of liquid samples prepared on a rack, performing a pretreatment such as a condensation according to necessity, and then injecting the samples into the mobile phase which has been supplied from the supply pump 11; a column 13 for temporally separating the liquid samples supplied with the mobile phase into components; a column oven 14 for controlling the temperature of the column 13; a detector 15 for detecting the sample components which have been separated by the column 13; and a preparative separation unit 16 for putting each component detected by the detector 15 into different containers. These units are controlled by a controller 18 based on the instructions from a personal computer (PC) 20.

One of the characteristic features of the present embodiment is a piping 17, which is provided between the detector 15 and the preparative separation unit 16 so as to delay the arrival of sample components from the detector 15 at the preparative separation unit 16 for a predetermined time. In addition, the controller 18 includes an execution time computation unit 19 for storing a point in time which serves as the base point for a processing in the preparative separation unit 16, and for computing the execution time of starting/finishing the preparative operation in the preparative separation unit 16 based on the base-point time and the shift time data which are added to the instruction of starting/finishing the preparative operation sent from the PC 20.

The operation control of each unit through the controller 18 and the data processing are performed by executing a dedicated data processing-operating program which has been installed in the PC 20. In the preparative separation system 1 of the present embodiment, the PC 20 functions not only as function blocks for ordinary data processing and operation control, but also as a delay time computation unit 21, a peak detection unit 22, and a shift time computation unit 23. The specific operations of the units 21 through 23 will be described later.

An input unit 24, which is an input device such as a keyboard and a mouse, and a display 25 such as a cathode ray tube (CRT) display or a liquid crystal display (LCD) are connected to the PC 20.

Hereinafter, the operation of the preparative separation system 1 of the present embodiment is described.

Before starting a preparative separation operation, a user provides the PC with a variety of parameters such as the temperature of the column and the flow rate of the pump. In the preparative separation system 1 of the present embodiment, the user also provides the volume of the piping 17 as another parameter. The delay time computation unit 21 computes the time required for a sample component to arrive at the preparative separation unit 16 from the detector 15 based on the volume of the piping 17 and the flow rate of the pump. Hereinafter, the period of time required for a sample component to arrive at the preparative separation unit 16 from the detector 16, which is computed by the delay time computation unit 21, will be referred to as the traveling time ta.

After all the parameters required for the preparative separation operation have been provided and an the instruction of starting the preparative separation operation is provided to the PC 20 by the user, the PC 20 instructs, through the controller 18, the auto sampler 12 to inject the sample. Upon receiving this instruction, the auto sampler 12 performs a predetermined pretreatment and injects the sample into the mobile phase. At the point in time when the sample is injected into the mobile phase, the auto sampler 12 informs the controller 18 of this event.

The controller 18 calculates, as the retention time, the time elapsed from the point in time when the sample was injected into the mobile phase (hereinafter, this time will be referred to as the "sample injection time"), adds the data of the retention time to each piece of the detection signal data which are continuously sent from the detector 15, and sends them to the PC 20. The execution time computation unit 19 stores the sample injection time as the base-point time. Hereinafter, the sample injection time (base-point time) will be denoted by Ts.

The peak detection unit 22 of the PC 20 creates a chromatogram based on the data of the detection signal and the retention time which are sent from the controller 18, and obtains the retention time when a peak is detected based on the level of the detection signal and the shape of upslopes and downslopes. In the following description, assume that the rise of a peak (initial point) has been detected at the retention time tb.

The shift time computation unit 23 adds the traveling time ta, which was computed in advance by the delay time computation unit 21, to the retention time tb. That is, $$tb'=ta+tb$$

is computed. The time tb' is a relative time based on the point in time at the retention time "0" (i.e. the sample injection time), and is independent of the time in the PC 20. Therefore, the time tb' itself can be used as the shift time for the point in time when the initiation of the preparative separation operation is executed.

The PC 20 sends a fractionation initiation operation instruction together with the shift time tb' to the controller 18.

When the controller 18 receives the fractionation initiation operation instruction from the PC 20, the execution time computation unit 19 adds the shift time tb' to the previously stored sample injection time Ts, and sets $$Tsb=Ts+tb'=Ts+ta+tb$$

as the execution time of the fractionation initiation operation in the preparative separation unit 16. The controller 18 stands-by by the execution time which has been set. At the execution time, the controller 18 makes the preparative separation unit 16 execute the fractionation initiation operation.

Rather than making the controller 18 stand-by the operation, the fractionation initiation operation may be instructed to the preparative separation unit 16 in advance designating the execution time.

Thus far, the process regarding the fractionation initiation operation has been described. The same or similar process may be taken for the fractionation termination operation.

In the preparative separation system 1 of the present embodiment, the PC 20 provides the execution time of the fractionation initiation/termination operation as a relative time to the controller 18. Therefore, even in the case where the time of the PC 20 and that of the controller 18 are not synchronized, the controller 18 can accurately set the execution time of fractionation initiation/termination operation which will be performed in the preparative separation unit 16. If the piping 17 is placed so that the traveling time of sample components is sufficiently larger than the delay time of signals due to the signal transfer lag and other reasons, the delay time can be absorbed, allowing the units to cooperate with each other at a correct timing.

Second Embodiment

An overlap injection data collection system 2, which is the second embodiment of the analyzing system according to the present invention, is described with reference to FIG. 2.

The overlap injection is a method in which, while a sample is being analyzed and before the analysis of this sample is completely finished, the next sample is injected from an auto sampler in order to increase the throughput of the analysis.

However, the pretreatment time by the auto sampler varies depending on the method settings, and the time required to inject a sample varies depending on the position of the vial and other factors. Therefore, it is difficult to predict when the sample is injected.

In addition, in a chromatograph analysis, a series of data processings as follows is usually performed for one sample: (1) data file creation, (2) data collection, (3) data file saving, (4) data analysis, and (5) report output. Performing an overlap injection causes a problem that the data processings for the two successive samples overlap each other, complicating the processing flow.

Figure 2:
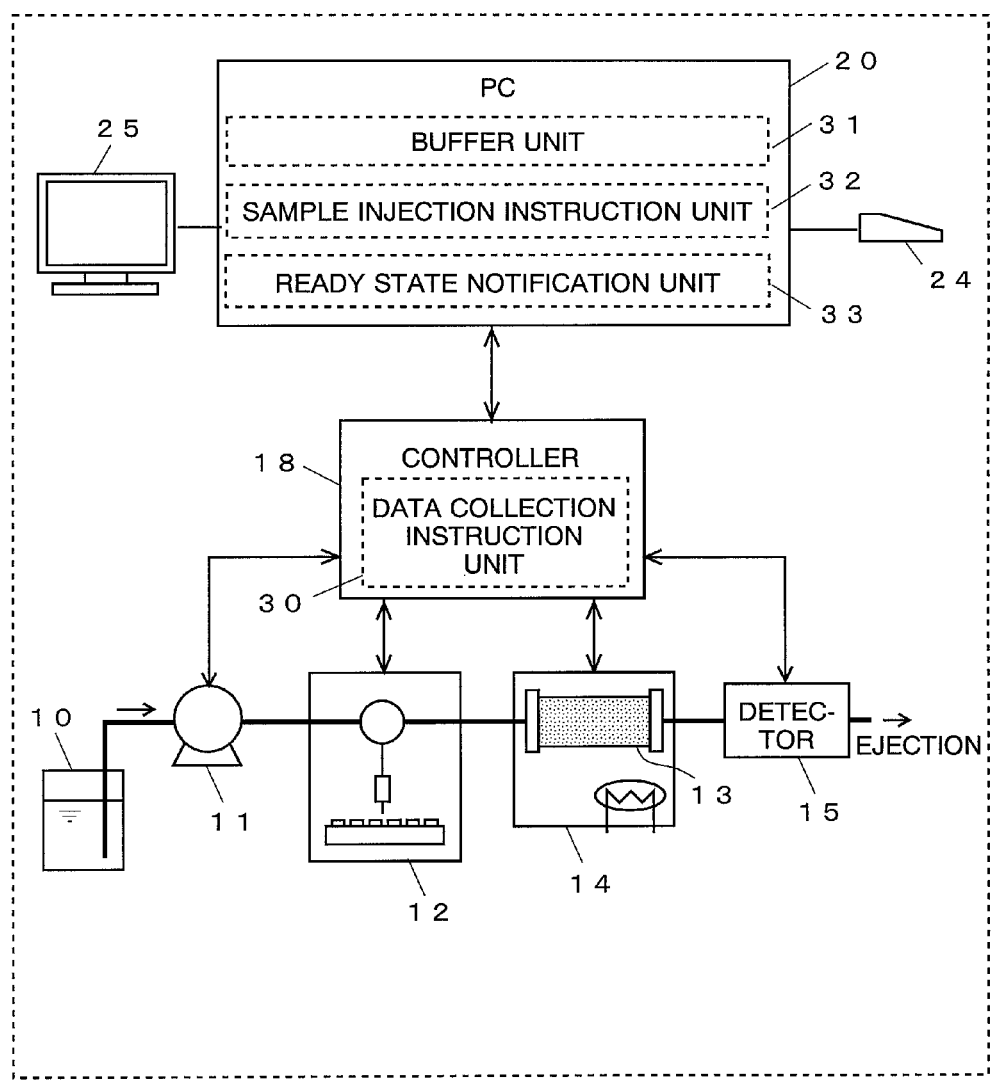
FIG. 2 is a schematic configuration diagram of the main components of the second embodiment of the analyzing system according to the preset invention.

FIG. 2 schematically shows the main components of the overlap injection data collection system 2 (which will be hereinafter simply referred to as the "system 2") of the present embodiment. The system 2 includes, as the units for performing a chromatograph analysis, a mobile phase container 10, a supply pump 10, an auto sampler (sample injector) 12, a column (separator) 13, a column oven 14, and a detector 15. These units are controlled by a controller 18 based on the instructions from a personal computer (PC) 20.

The controller 18 has a data collection instruction unit 30 for instructing the PC 20 at a predetermined timing to start collecting the data of the next sample.

The PC 20 controls each unit through the controller 18 and performs a data processing by executing a dedicated data processing-controlling program which has been installed in the PC 20. In the system 2 of the present embodiment, the PC 20 functions not only as function blocks for data processing and operation control for a conventional overlap injection, but also as a buffer unit 31, a sample injection instruction unit 32, and a ready state notification unit 33. The specific operations of the units 31 through 33 will be described later.

An input unit 24, which is an input device such as a keyboard and a mouse, and a display 25 such as a cathode ray tube (CRT) display or a liquid crystal display (LCD) are connected to the PC 20.

Hereinafter, the operation of the system 2 of the present embodiment will be described with reference to FIG. 3, which is an explanation diagram of the processing by the system 2. FIG. 3 shows the case where the analyses of samples A and B overlap each other. With the point in time when each sample is injected being designated as 0, it is possible to predict from the analysis conditions and other factors that no peak appears between the time 0 and t0 and peaks appear only between the time t0 and te.

Before starting an analysis, a user provides the PC with a variety of parameters such as the temperature of the column and the flow rate of the pump. After all the analysis conditions are provided and the user instructs the PC 20 to start the analysis, the PC 20 first creates a data file for the sample A. Then, the PC 20 instructs the auto sampler 20 to inject the sample. Upon receiving this instruction, the auto sampler 12 performs a predetermined pretreatment, and injects the sample A into the mobile phase. At the point in time when the sample is injected into the mobile phase, the auto sampler 12 informs the controller 18 of this event.

The controller 18 sets the point in time when the sample A was injected into the mobile phase as T=0, calculates the time elapsed from that point in time, adds the data of the elapsed time T to each piece of the detection signal data which are continuously sent from the detector 15, and sends them to the PC 20. The data of the detection signal and those of the elapsed time T (which will hereinafter be referred to as the "detection data") are temporarily stored in the buffer unit 31.

The PC 20 sequentially reads the detection data stored in the buffer unit 31 from the point in time T=0, and writes the data one after another in the data file created for the sample A (FIG. 3).

At the point in time of T1=te−t0, the sample injection instruction unit 32 instructs the auto sampler 12 through the controller 18 to inject the next sample B. The auto sampler 12 performs a predetermined pretreatment to the sample B and injects the sample B into the mobile phase (at the point in time of "INJ" in FIG. 3). When the sample B is injected into the mobile phase, the auto sampler 12 informs the controller 18 of this injection. The data collection instruction unit 30 of the controller 18 receives this notification and memorizes the point in time of the injection.

Even after the injection of the sample B, the PC 20 continues to write the data in the data file for the sample A through the buffer unit 31, and finishes writing the data at the point in time of T2=te. Then, the PC 20 performs the processings such as saving the data file, analyzing the data, and outputting a report.

After finishing the report output for the sample A, the PC 20 creates a data file of the sample B. Then, the PC 20 sends a ready state notification, which signifies that the preparation for the data collection of the sample B has been finished, to the data collection instruction unit 30 of the controller 18 from the ready state notification unit 33.

Upon receiving the ready state notification, the data collection instruction unit 30 computes the period of time (i.e. ts) elapsed from the point in time when the sample B was injected (at the point in time of the retention time 0 of the sample B) to the point in time when the data collection instruction unit 30 received the ready state notification (assuming that this point in time is at the retention time ts of the sample B). The data collection instruction unit 30 adds the instruction of data collection operation for the sample B and the elapsed time ts from the injection of the sample B to the data of the detection signal at this point in time as well as the data of the elapsed time T (=T3), and sends these data to the PC 20.

Upon receiving the instruction of data collection operation from the data collection instruction unit 30, the PC 20 reads out the detection data between the point in time going back by the time period is from the elapsed time T3 (i.e. T3−ts) of the detection signal, which have been sent together with the instruction, and the point in time of T3, and then writes the data in the data file for the sample B (the hatched area in FIG. 3). After that, the PC 20 continues to write the data after the point in time T3 in the data file through the buffer unit 31 as in the conventional manner This operation is performed by the point in time of T5=T3−ts+te so that the time period of the written data corresponds to the retention time to of the sample B. Then, the PC 20 finishes writing the data for the sample B in the data file, saves the data file, analyzes the data, and outputs a report.

If there is a sample (e.g. sample C) to be measured after the sample B, the sample injection instruction unit 32 provides the instruction of injecting the sample C at the point in time of T4=T3−ts+te−t0, which corresponds to the retention time te−t0 of the sample B. Then, the same operation as for the sample B will be performed.

As just described, the present system 2 can perform a series of operations for one sample such as: (1) creating a data file, (2) writing data, (3) saving the data file, (4) analyzing the data, and (5) outputting a report, while performing an overlap injection. These operations can be performed without overlapping the operations for another sample, and the order of the series of operations can remain unchanged for the next sample to be analyzed.

The analyzing system according to the present invention has been described by using embodiments. It should be noted that the embodiments described thus far are merely an example, and it is evident that any appropriate modification, adjustment, or addition can be made within the spirit of the present invention.

In the second embodiment, the instruction of injecting the next sample is performed by the sample injection instruction unit 32 at the point in time of the retention time te−t0 of the sample that is being analyzed. However, taking into consideration the time required for the pretreatment in the auto sampler 12, the injection instruction may be provided at an earlier timing. Although it is difficult to previously know the time for a pretreatment because it varies depending on the sample, it is possible to predict the minimum time required for the pretreatment. Therefore, providing the injection instruction earlier by the minimum time can increase the throughput of the analysis.

EXPLANATION OF NUMERALS

1 . . . Preparative Separation System
2 . . . Overlap Injection Data Collection System
10 . . . Mobile Phase Container
11 . . . Supply Pump
12 . . . Auto Sampler (Sample Injector)
13 . . . Column (Separator)
14 . . . Column Oven
15 . . . Detector
16 . . . Preparative separation unit
17 . . . Piping
18 . . . Controller
19 . . . Execution Time Computation Unit
20 . . . Personal Computer (PC)
21 . . . Delay Time Computation Unit
22 . . . Peak Detection Unit
23 . . . Shift Time Computation Unit
24 . . . Input Unit
25 . . . Display
30 . . . Data Collection Instruction Unit
31 . . . Buffer Unit
32 . . . Sample Injection Instruction Unit
33 . . . Ready State Notification Unit

The invention claimed is:

1. An analyzing system, comprising:
a sample injector for performing an overlap injection in which while a sample is being analyzed a next sample is injected;
a separation unit for continuously separating the sample and the next sample into different components;
a detector for continuously detecting the separated sample components of the sample and the next sample and for providing detection data;
a data collection instruction unit;
a buffer unit for sequentially memorizing detection data for the sample and the next sample provided from the detector;
a data processing unit for sequentially collecting detection data of the sample and the next sample from the buffer unit and performing a predetermined data processing for the detection data;
a sample injection instruction unit for instructing the sample injector to inject the next sample at a predetermined point in time; and a ready state notification unit for notifying the data collection instruction unit, when the data processing unit has finished the predetermined data processing for the detection data of the sample obtained from the buffer unit, that a preparation for a data collection of the next sample memorized in the buffer unit has been finished, wherein the data collection instruction unit sends, upon receiving the notification from the ready state notification unit, an elapsed time from a point in time when the aforementioned next sample was injected to a point in time when the notification was received together with an instruction of data collection of the aforementioned next sample to the data processing unit, and the data processing unit reads out, upon receiving the instruction of data collection, from the buffer unit the data of the aforementioned next sample detected by the detector from a point in time going back by the elapsed time from the point in time of the instruction of data collection from the data collection instruction unit and memorized in the buffer unit, writes the data in a data file, and initiates the aforementioned data processing.

\* \* \* \* \*